United States Patent [19]

Kantrowitz et al.

[11] Patent Number: 4,692,148
[45] Date of Patent: Sep. 8, 1987

[54] INTRA-AORTIC BALLOON PUMP APPARATUS AND METHOD OF USING SAME

[75] Inventors: Adrian Kantrowitz, Pontiac; Paul S. Freed, Bloomfield Hills, both of Mich.; Hiroyuki Tachi, Tokyo; Akira Suzuki, Nishio, both of Japan

[73] Assignee: Aisin Seiki Kabushiki Kaisha, Kariya, Japan

[21] Appl. No.: 845,557

[22] Filed: Mar. 28, 1986

[51] Int. Cl.⁴ .............................................. A61M 29/00
[52] U.S. Cl. ..................................... 604/96; 128/696
[58] Field of Search ................... 604/96, 93; 128/1 R, 128/1 D, 696

[56] References Cited

U.S. PATENT DOCUMENTS

| 3,081,765 | 3/1963 | Kompelien . |
| 3,533,403 | 10/1970 | Woodson . |
| 3,553,625 | 1/1971 | Stedman . |
| 3,585,983 | 6/1971 | Kantrowitz et al. . |
| 3,707,960 | 1/1973 | Freed . |
| 3,896,803 | 7/1975 | Mason . |
| 3,913,565 | 10/1975 | Kawahara . |
| 4,077,394 | 3/1978 | McCurdy . |
| 4,148,319 | 4/1979 | Kasper et al. . |
| 4,191,193 | 3/1980 | Seo . |
| 4,274,423 | 6/1981 | Mizuno et al. . |
| 4,362,150 | 12/1982 | Lombardi, Jr. et al. . |
| 4,552,127 | 11/1985 | Schiff . |
| 4,569,332 | 2/1986 | Schiff et al. . |
| 4,592,340 | 6/1986 | Boyles ................................... 604/96 |
| 4,619,247 | 10/1986 | Inoue et al. ....................... 604/96 X |

FOREIGN PATENT DOCUMENTS

995751 2/1983 U.S.S.R. .

Primary Examiner—John D. Yasko
Attorney, Agent, or Firm—Finnegan, Henderson, Farabow, Garrett & Dunner

[57] ABSTRACT

An apparatus and method for placing an aortic balloon catheter is provided wherein a pair of spaced electrodes on the distal end of the catheter assembly are disposed inside a thoracic aorta near a patient's heart and are used to sense R-waves and P-waves in an ECG signal. The electrodes are moved to an ideal intra-aortic position where the R-waves and P-waves are sensed to have the same magnitude. The P-wave, occurring earlier than the R-wave, serves to accurately predict theoccurrence of the R-wave. The balloon of the catheter is deflated upon sensing the R-wave.

9 Claims, 8 Drawing Figures

INTRA-AORTIC BALLOON PUMP APPARATUS AND METHOD OF USING SAME

BACKGROUND OF THE INVENTION

This invention relates to a method of accurately sensing diastolic and systolic motion of a heart, an intra-aortic balloon appartus for inflating and deflating a balloon introduced into the aorta in the vicinity of the heart, and a method of disposing the balloon apparatus at the proper intra-aortic position.

It is well-known in the art, as described in, for example the specification of U.S. Pat. No. 4,362,150. to provide cardiac assistance by introducing a balloon into the thoracic aorta of a patient and causing the balloon to inflate and deflate in accordance with the motion of the patient's heart. A balloon of this type is made to inflate during diastole and deflate during systole. This reduces the load on the left ventricle and raises aortic pressure to increase the blood flow to the coronary and carotid arterics. It is therefore essential that cardiac motion be sensed accurately to enable the balloon to be inflated and deflated correctly in accordance with the cardiac cycle.

Methods of sensing cardiac motion include measurement of aortic pressure and measurement based on an electrocardiographic signal. It has been attempted to combine means for effecting such measurements with the aforementioned intra-aortic balloon apparatus. One example in which an intra-aortic balloon is manipulated while aortic pressure is measured is disclosed in the specification of U.S. Pat. No. 4,077,394, which teaches to inflate the balloon for a prescribed period of time that begins at the occurrence of the dicrotic notch. However, since the disclosed method requires that the aortic blood be withdrawn from the patient through a central tube that passes through the balloon in order that the pressure of the blood may be measured extracorporeally, there is a time delay between actual motion of the patient's heart and a measured value showing the actual motion thereof. Moreover, though the balloon is inflated at the dicrotic notch, the occurrence of the dicrotic notch must first be verified. Owing to the time delay, however, verification of the dicrotic notch lags behinds actual occurrence, with the result that there is a tendency for the balloon to be inflated later than actually required. Additionally, the measured pressure is distorted due to the presence of the long tube, and has motion artifact added to it, both of which made consistent detection of the dicrotic notch difficult. A method of inflating and deflating the balloon based on an ECG signal is set forth in the specification of U.S. Pat. No. 3,707,960. Here two electrodes are arranged at either end of the balloon, the electrodes sense the ECG signal, and the balloon is inflated and deflated in dependence upon a R-wave contained in the signal. The problem with this method is that in some patients the balloon should be deflated prior to the detection of the R-wave thus necessitating prediction of its occurence.

Other shortcoming common to the prior art include problems in correctly disposing the balloon within the thoracic aorta.

SUMMARY OF THE INVENTION

Accordingly, an object of the present invention is to solve the aforementioned problems encountered in the prior art.

Another object of the present invention is to provide a novel method of accurately sensing P- and R-waves of an ECG signal.

Still another object of the present invention is to provide a method of accurately placing an intra-aortic balloon in an aorta while sensing P- and R-waves of in ECG signal.

A further object of the present invention is to provide a method of deflating an intra-aortic balloon in response to a P-wave in an ECG signal and inflating the intra-aortic balloon prior to the occurrence of a dicrotic notch in aortic pressure.

A further object of the present invention is to provide an apparatus suitable for practicing the foregoing methods.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 3(a), (b) (c) are waveform diagrams showing P- and R-waves the states of which depend upon the position of the electrodes in the aorta;

DESCRIPTION OF THE PREFERRED EMBODIMENTS

Before describing the present invention in detail, reference will be made to FIGS. 1, 2 and 3, which are useful in understanding the principle of the invention.

Figure 1:
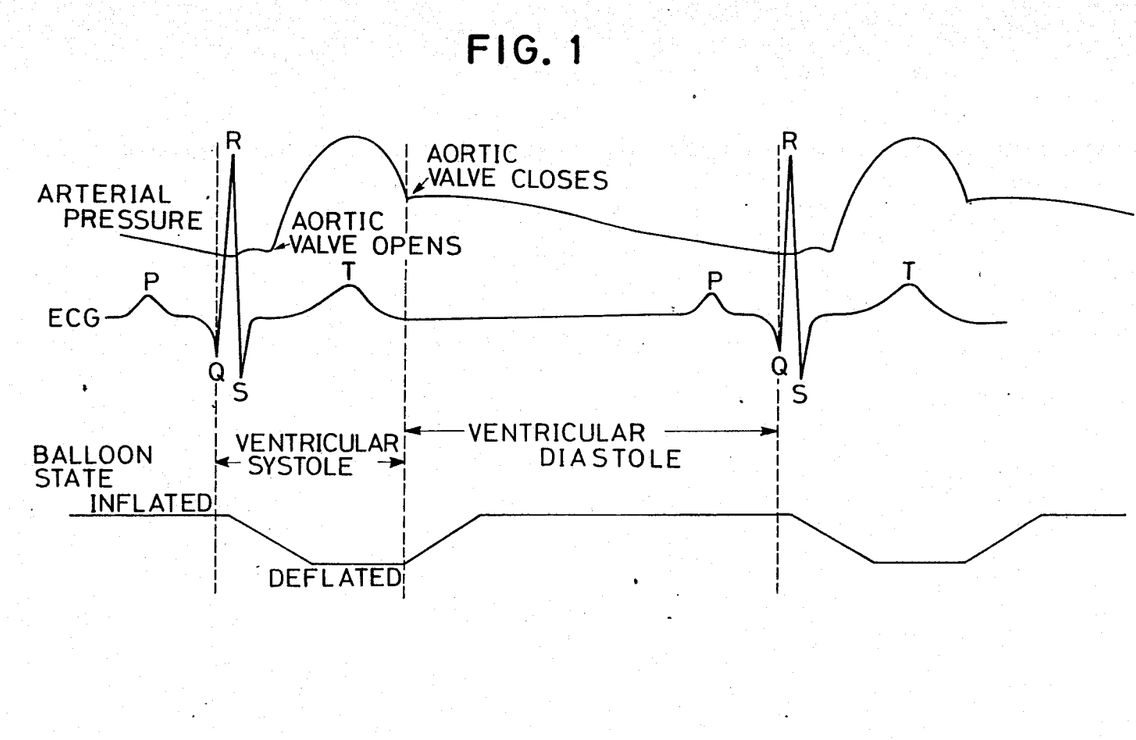
FIG. 1 is a view showing the relationship of aortic blood pressure, ECG and balloon state.

It is evident from FIG. 1, which shows how aortic blood pressure, ECG and balloon state are related, that the R-wave of the ECG occurs after the P-wave. The R-wave gives advance notice of the opening of the aortic valve, and the dicrotic notch appears in the aortic pressure at closure of the aortic valve. Accordingly, the balloon, following its insertion into the aorta, is deflated in response to the R-wave and inflated after the occurrence of the dicrotic notch. It is thus necessary to accurately predict when the R-wave will occur and to deflate the balloon in synchronism with the R-wave. To this end, the inventors have taken note of the significance of the P-wave, which precedes the occurrence of the R-wave, and has considered predicting the occurrence of the R-wave by first accurately sensing the P-wave. However, since the P-wave has but a very small peak in conventional ECG measurement, difficulty is experienced in discriminating between the P-wave and noise. Verification of a distinct P-wave is particularly difficult to achieve in emergency cases where rapid treatment of a patient is required.

Figure 2:
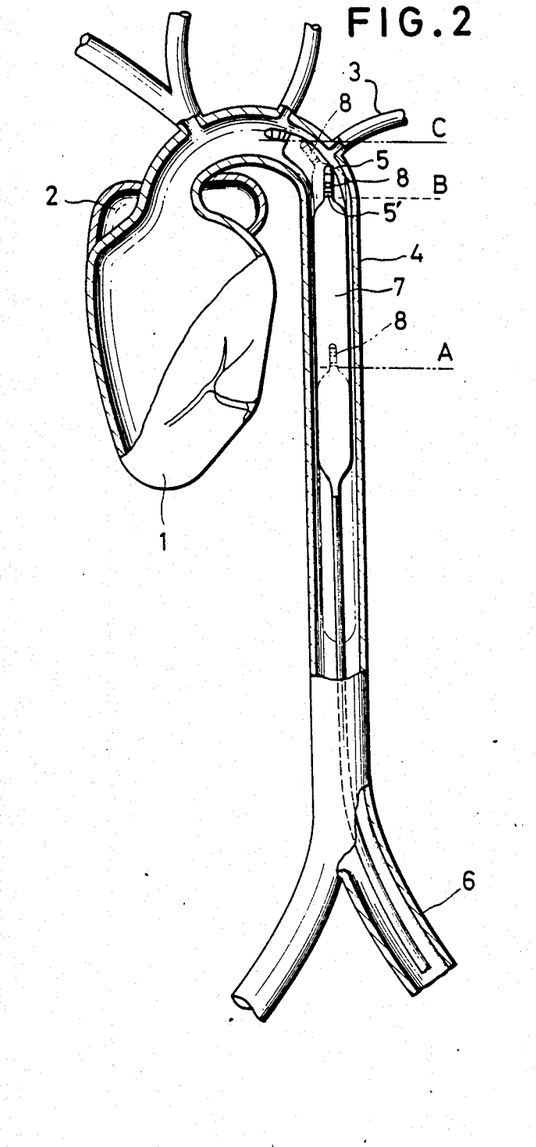
FIG. 2 is a partial sectional view of the vicinity of a human heart and shows electrodes disposed in the patient's aorta.
Figure 3:
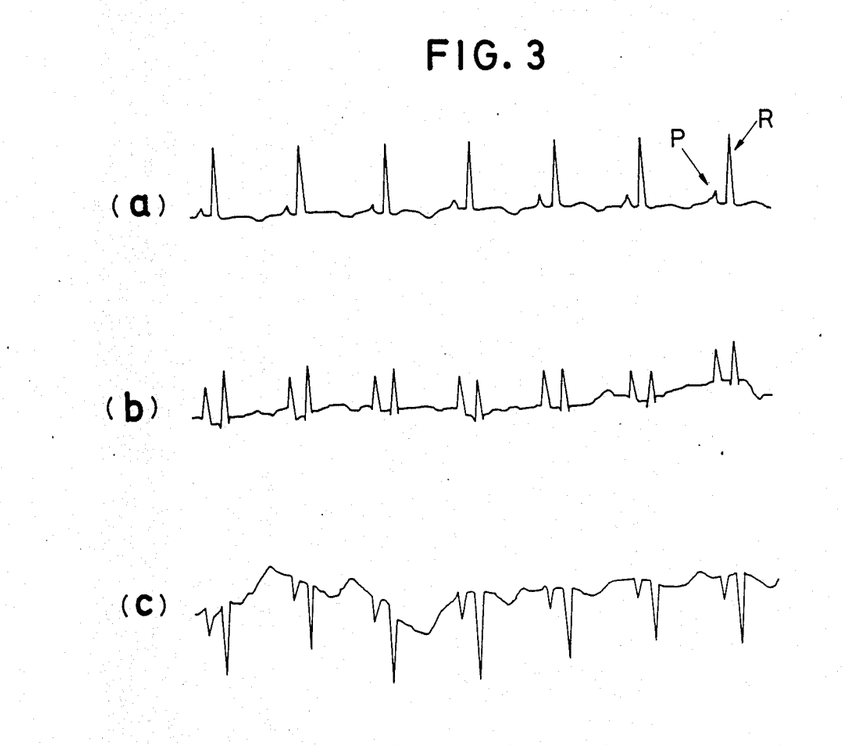

FIG. 2 shows an electrode pair placed in a patient's aorta in the vicinity of the heart. Numeral 1 denotes the ventricle, 2 the atrium, 3 the subclavian arteries, and 4 the aorta. An electrode pair 5,5'5" is introduced into the aorta through the femoral artery 6 by percutaneous or surgical means. With the electrodes 5 located at position A in FIG. 2, a R-wave having a high peak is sensed, but the P-wave is small difficult to verify, as shown in FIG. 3(a). Moving the electrodes 5 to the B position in FIG. 2 results in detection of the P- and R-waves as waveforms of substantially the same size, as shown in FIG. 3(b). When the electrodes 5 are inserted further toward the C position in FIG. 2, first the P- and the R-waves undergo a polarity inversion, as depicted in FIG. 3(c). Therefore, in accordance with the present invention, the electrodes 5, 5' are introduced into the aorta 4, and obtained by them the electrocardiogram is monitored. The electrodes 5, 5' are advanced further into the aorta 4 if the waveform produced is as shown in FIG. 3(a), and are withdrawn an appropriate amount if the waveform obtained is as shown in FIG. 3(c), with the object being to eventually dispose the electrodes 5, 5' and the balloon 7 at an optimum intra-aortic position, namely position B, such that the tip of balloon pump lies within 2 cm of the origin of the left subclavian artery. As a result, the P-wave can be sensed in an accurate fashion, thereby enabling the occurrence of the R-wave to be predicated so that the balloon may be deflated in synchronism with the R-wave.

A pressure transducer 8 is arranged near the pair of electrodes 5,5' for sensing the aortic blood pressure which enables detection of the dicrotic notch (see FIG. 1), so that the balloon 7 may be inflated in dependence upon the occurrence of the dicrotic notch.

Inflation and deflation of the balloon 7 may be controlled by various computerized means. One example is to feed the P- and R-wave signals into a computer, which would be programmed to control a gas feed mechanism so as to discharge helium gas from the interior of the balloon 7 in synchronism with the R-wave to deflate the balloon, feed helium gas into the balloon 7 after a prescribed period of time to inflate the balloon, and then discharge the gas in response to the next R-wave signal. The computer would repeat these steps in the manner described. Another example is to feed the P- and R-waves and a signal indicative of the dicrotic notch into a computer, which would be programmed to control a gas feed mechanism so as to discharge the gas from the balloon 7 in synchronism with the R-wave and feed gas into the balloon 7 in synchronism with the occurrence of the dicrotic notch.

Figure 4:
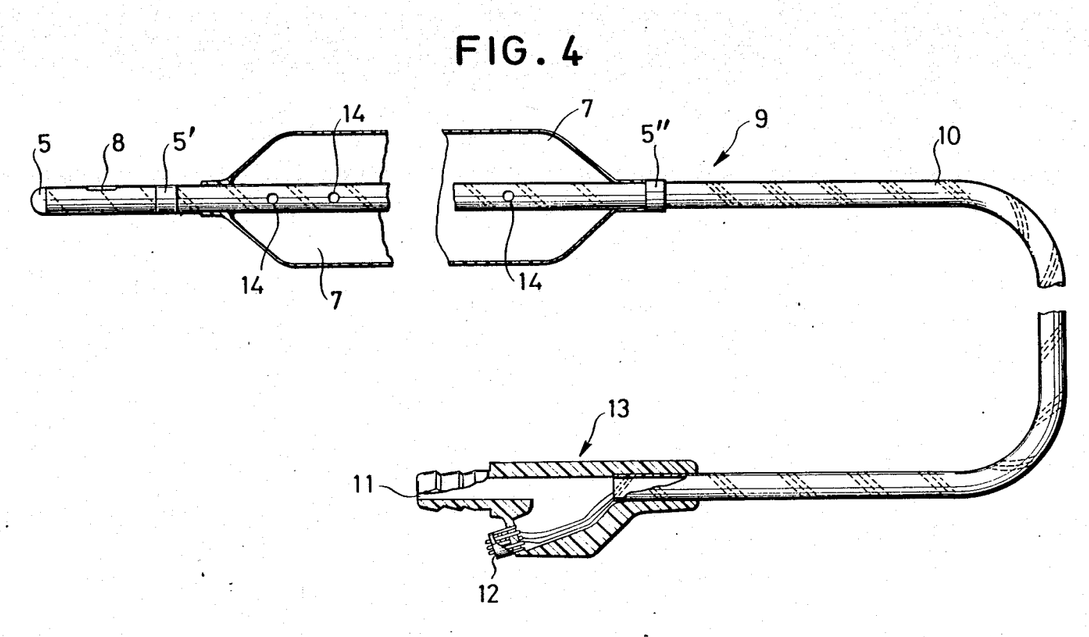
FIG. 4 is a sectional view illustrating an embodiment of an intra-aortic balloon apparatus according to the present invention.

An embodiment of an intra-aortic balloon apparatus practicing the foregoing method of the present invention is indicated generally at numeral 9 in FIG. 4. The balloon 7 is provided with a soft and flexible, slender tube-like catheter 10 that passes through the interior of the balloon 7, the distal end of the catheter 10 extending beyond the distal end of the balloon 7. The catheter 10 has a proximate end to which is secured a coupling 13 having a gas supply port 11 and electric terminals 12. The catheter 10 defines an internal passageway and its wall is perforated with a plurality of small holes 14 at the portion thereof to which the balloon 7 is attached. The gas supply port 11 and the interior of the balloon are thus communicating via the small holes 14 and the passageway inside the catheter 10. The balloon 7 is inflated and deflated by controlling the inflow and outflow of gas to and from the gas supply port 11.

The electrode pair 5,5' disposed at the distal end of the catheter 10 protruding from the distal end of balloon 7. The pressure transducer 8 is disposed between the electrodes 5,5' which are spaced apart by about 2 cm. Attached to the catheter 10 at the proximate end of the balloon 7 is an additional electrode 5". Lead wires connected at their one ends to the electrodes 5, 5', 5" and to the pressure transducer 8 are wound in helical form along the inner wall surface of the catheter 10 and extend into the coupling 13 where they are connected at their other ends to the terminals 12.

The intra-aortic balloon apparatus 9 having the foregoing construction is inserted into the aorta through the femoral artery by surgical introduction and senses the P- and R-waves via the electrodes 5, 5' or 5". The apparatus is disposed at an intra-aortic position at which the sensed P- and R-waves will be of approximately the same magnitude, as described earlier. Withdrawal of the gas from the balloon 7 is synchronized to the R-wave signal from the electrodes 5, 5' and feed of gas to the balloon 7 is synchronized with the dicrotic notch signal from the pressure transducer 8.

Another embodiment of an intra-aortic balloon apparatus according to the present invention will now be described with reference to FIG. 5. The apparatus, shown generally at numeral 9', includes a tubular first catheter 15 having a proximate end joined to a Y-shaped connector 16 and a distal end supporting a proximate end of the balloon 7 air-tightly. A central tubular member 17 extends through the interior of the first catheter 15 and has a distal end of comparatively larger diameter projecting from the distal end of first catheter 15 and air-tightly supporting the distal end of the balloon 7. The central tubular member 17 has a proximate end fixedly secured to a rotary member 18 having a portion in threaded engagement with the connector 15. Turning the rotary member 18 with respect to the connector 16 rotates the tubular member 17 so that the balloon 7 may be wrapped around the tubular member 17 by rotating the same in one direction and unwrapped from the tubular member 17 by rotating same in the opposite direction. The connector 16 has a port 19 from which a fluid such as helium gas is introduced from an external source, not shown. The gas is fed from connector 16 into the balloon 7 through a passageway defined between the inner surface of first catheter 15 and the outer surface of tubular member 17, whereby the balloon 7 is made to inflate. Withdrawing the gas from the balloon through the same passageway causes the balloon to deflate.

A tubular second catheter 20, the diameter whereof is smaller than that of the first catheter 15, is capable of being passed through the passageway of the central tubular member 17 and has a distal end that projects from the distal end of the tubular member 17. The second catheter 20 has a proximate end secured to a second connector 21. The second connector 21 has a tapered distal end portion 22 lockably fitted into a tapered bore formed inside the rotary member 18. A knob 23 is provided for releasably locking the second connector 21 to the rotary member 18.

The electrode pair 5, 5' and pressure transducer 8 are disposed at the distal end portion of the second catheter 20. The lead wires from the electrodes 5, 5' and transducer 8 are wound in helical fashion along the inner wall surface of the second catheter 20 and are connected to terminals in the second connector 21. The second connector 21 is in turn connected to arithmetic circuitry, not shown, the function whereof is described hereinbelow.

Figure 5:
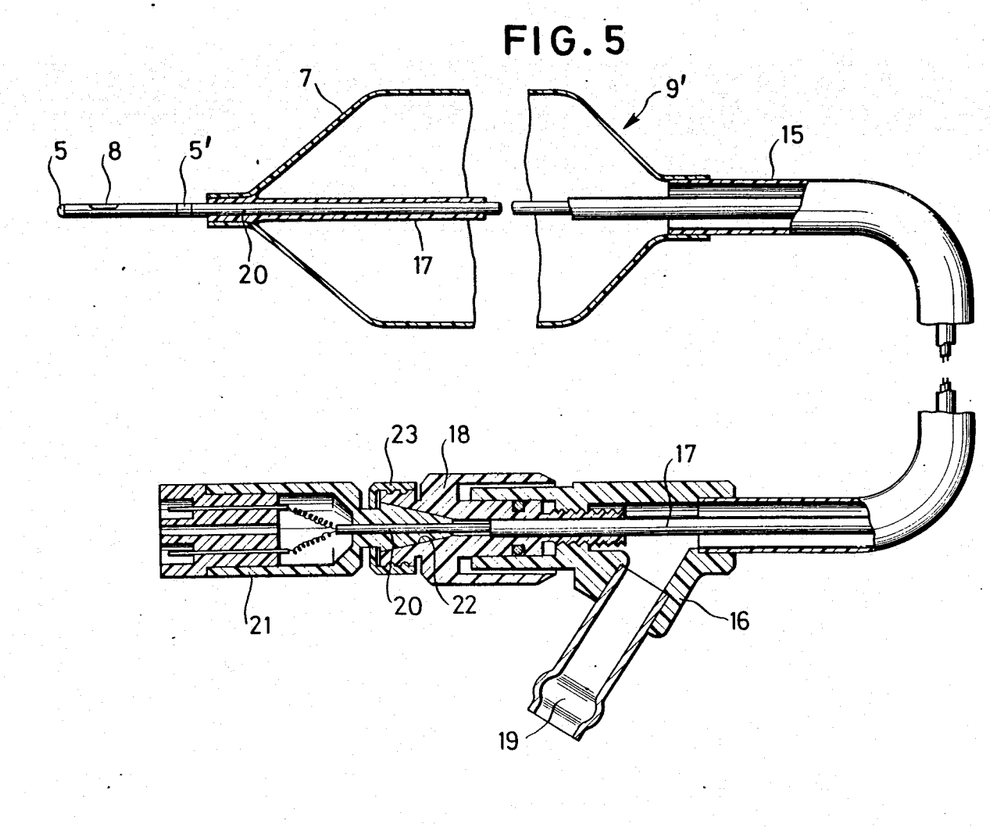
FIG. 5 is a sectional view illustrating another embodiment of an intra-aortic balloon apparatus according to the present invention.

To use the intra-aortic balloon apparatus 9' shown in FIG. 5, a guide wire, not shown, is inserted into the aorta from the patient's femoral region as by the Seldinger method and is passed along the aorta until the leading end of the guide wire reaches the vicinity of the patient's heart. Next, the other end of the guide wire is inserted into the passageway of tubular member 17, into which the second catheter 20 has not yet been introduced. The tubular member 17, with the balloon 7 wrapped around it, is then introduced together with the first catheter 15 into the aorta while being guided along the guide wire. When these have reached a predetermined position inside the aorta, the guide wire is withdrawn from the patient's body through the passageway in tubular member 17. This is followed by inserting the distal end of the second catheter 20 into the tubular member 17 and then introducing the distal end of the second catheter 20 into the aorta through the tubular member 17 while manipulating the connector 21 to which the second catheter 20 is affixed. The tapered distal end portion 22 of second connector 21 is brought into abutting contact with the rotary member 18 and the knob 23 is turned to lock the second connector 21 and rotary member 18 together. The connector 21 is connected to the aforementioned arithmetic circuit, not shown, and the electrodes 5, 5' at the distal end of the second catheter 20 sense the P- and R-waves. The resulting signals are monitored so that the balloon 7 may be moved to the correct intra-aortic position by manipulating the connector 21. Thus, the balloon 7 has thus been moved to the correct position.

The aforementioned arithmetic circuit receives the P- and R-wave signals from the electrodes 5, 5' and the aortic pressure signal from the pressure transducer 8 to calculate the counterpulsation timing in accordance with these signals. The balloon 7 is caused to inflate and deflate at the timing calculated.

Figure 6:
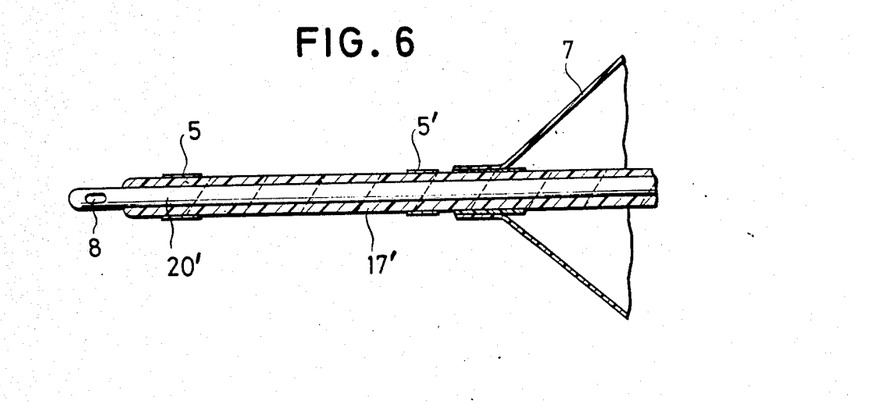
FIG. 6 is a partial sectional view illustrating a third embodiment of an intra-aortic balloon apparatus according to the present invention.

In an embodiment of the intra-aortic balloon apparatus shown in FIG. 5, the distal end of the tubular member, indicated at numeral 17', is extended beyond the distal end of balloon 7, and the electrodes 5, 5' are disposed on the extended portion of the tubular member 17'. The pressure transducer 8, on the other hand, is attached to the distal end of the second catheter, here shown at numeral 20'. With this arrangement, the second catheter 20' need not be used if measurement of aortic blood pressure is unnecessary. In such case, the electrodes 5 sense the P- and R-waves and the balloon 7 is disposed at the correct intra-aortic position, deflated in response to the R-wave and inflated upon passage of a prescribed period of time. Note that the lead wires from the electrodes 5, 5' are imbedded in the wall of the tubular member 17' and may be connected to the Y-shaped first connector 15 (FIG. 5) so that the signals from the electrodes 5, 5' may be extracted from the connector 16. When the second catheter 20' is not used, a plug (not shown) is fitted into the rotary member 18 in place of the connector 21.

It will be evident from the foregoing description that the present invention makes it possible for the balloon to be inflated and deflated in correct response to the actions of the patient's heart, and that the invention enables the balloon to be disposed at the proper intra-aortic position with greater precision.

As many apparently widely different embodiment of the present invention can be made without departing from the spirit and scope thereof, it is to be understood that the invention is not limited to the specific embodiments thereof except as defidned in the appedned claims.

What is claimed is:

1. A method of disposing a balloon inside an aorta, comprising the steps of:
   disposing at least a pair of spaced electrodes inside a thoracic aorta near a patient's heart;
   sensing a R-wave and a P-wave by said electrodes, and
   using the P-wave and R-wave morphologies and their related magnitude to determine the optimal placement of the balloon pump, as close as possible to the atria.

2. The method according to claim 1, wherein the balloon is deflated prior to the occurence of the R-wave following sensing of the P-wave.

3. A method of disposing a balloon inside as aorta, comprising the steps of:
   disposing at least a pair of spaced electrodes and at least one pressure transducer inside a thoracic aorta near a patient's heart;
   sensing a R-wave and a P-wave by said electrodes,
   inserting a balloon into the throracic aorta up to a position at which the R- and P-waves are equal in magnitude; and
   deflating the balloon when the R-wave occurs following sensing of the P-wave, sensing a dicrotic notch in aortic blood pressure by said pressure transducer, and inflating the balloon in response to sensing of the dicrotic notch.

4. An intra-aortic balloon apparatus comprising:
   a tubular catheter assembly having a distal end and a proximate end, said proximate end being fixedly sucured to a coupling having a gas feed port for feeding a gas into said catheter;
   a balloon provided on said catheter assembly at the distal end thereof for receiving the gas fed into said catheter assembly, said balloon having a distal end and a proximate end;
   said catheter assembly and said balloon interiorly defining a passageway for the gas;
   at least a pair of electrodes provided on the distal end of said catheter assembly; and
   electrical terminals provided on the coupling and adapted to receive electric signals from said electrodes.

5. The apparatus according to claim 4, wherein said catheter assembly comprises:
   a first catheter having a distal end fixedly secured to the proximate end of said balloon and a proximate end fixedly secured to the coupling;
   a tubular member passing through said first catheter and having a distal end fixedly secured to the distal end of said balloon and a proximate end fixedly secured to a knob provided on the coupling; and
   a second catheter freely insertable into said tubular member and having a distal end for being projected from the distal end of said tubular member and on which said electrodes are disposed.

6. The apparatus according to claim 4, wherein said catheter assembly comprises:
   a catheter having a distal end fixedly secured to the proximate end of said balloon and a proximate end fixedly secured to the coupling, and
   a tubular member passing through said catheter, said tubular member having a distal end fixedly secured to the distal end of said balloon and projecting therefrom, and a proximate end fixedly secured to a knob provided on the coupling, said electrodes being disposed on the distal end of said tubular member projecting from the distal end of said balloon.

7. An intra-aortic balloon apparatus comprising:
a tubular catheter assembly having a distal end and a proximate end, said proximate end being fixedly secured to a coupling having a gas feed port for feeding a gas into said catheter;
a balloon provided on said catheter assembly at the distal end thereof for receiving the gas fed into said catheter assembly, said balloon having a distal end and a proximate end;
said catheter assembly and said balloon interiorly defining a passageway for the gas;
at least a pair of electrodes provided on the distal end of said catheter assembly;
a pressure transducer provided on the distal end of said catheter assembly; and
electrical terminals provided on the coupling and adapted to receive electric signals from said electrodes and said pressure transducer.

8. The apparatus according to claim 7, wherein said catheter assembly comprises:
a first catheter having a distal end fixedly secured to the proximate end of said balloon and a proximate end fixedly secured to the coupling;
a tubular member passing through said first catheter and having a distal end fixedly secured to the distal end of said balloon and a proximate end fixedly secured to a knob provided on the coupling; and
a second catherer freely insertable into said tubular member and having a distal end for being projected from the distal end of said tubular member and on which said electrodes and said pressure transducer are disposed.

9. The apparatus according to claim 7, wherein said catheter assembly comprises:
a first catheter having a distal end fixedly secured to the proximate end of said balloon and a proximate and fixedly secured to the coupling,
a tubular member passing through said first catheter, said tubular member having a distal end fixedly secured to the distal end of said balloon and projecting therefrom, and a proximate end fixedly secured to a knob provided on the coupling; and
a second catheter freely insertable into said tubular member and having a distal end for being projected from the distal end of said tubular member;
said electrodes being disposed on the distal end of said tubular member projecting from the distal end of said balloon;
said pressure transducer being disposed on the distal end of said second catheter.

* * * * *

UNITED STATES PATENT AND TRADEMARK OFFICE
CERTIFICATE OF CORRECTION

PATENT NO.   :   4,692,148

DATED        :   September 8, 1987

INVENTOR(S)  :   Adrian Kantrowitz et al.

It is certified that error appears in the above-identified patent and that said Letters Patent is hereby corrected as shown below:

In Abstract, line 9, change "theoccurrence" to -- the occurrence --;

Claim 2, column 6, line 15, change "occurence" to -- occurrence --;

Claim 4, column 6, line 34, change "sucured" to -- secured --; and

Claim 8, column 8, line 5, change "catherer" to -- catheter --.

Signed and Sealed this

Second Day of February, 1988

*Attest:*

DONALD J. QUIGG

*Attesting Officer*            *Commissioner of Patents and Trademarks*